US007109519B2

(12) United States Patent
Gerlach

(10) Patent No.: US 7,109,519 B2
(45) Date of Patent: Sep. 19, 2006

(54) BIS(2-ACENYL)ACETYLENE SEMICONDUCTORS

(75) Inventor: Christopher P. Gerlach, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 525 days.

(21) Appl. No.: 10/620,027

(22) Filed: Jul. 15, 2003

(65) Prior Publication Data
US 2005/0012090 A1     Jan. 20, 2005

(51) Int. Cl.
H01L 35/24 (2006.01)
H01L 51/00 (2006.01)
(52) U.S. Cl. .......................... 257/40; 552/271; 585/26
(58) Field of Classification Search ............. 257/40; 552/271; 585/26
See application file for complete search history.

(56) References Cited

U.S. PATENT DOCUMENTS

| | | | |
|---|---|---|---|
| 5,347,144 | A | 9/1994 | Garnier et al. |
| 5,956,679 | A | 9/1999 | Komori et al. |
| 6,215,130 | B1 | 4/2001 | Dodabalapur |
| 6,265,243 | B1 | 7/2001 | Katz et al. |
| 6,288,188 | B1 | 9/2001 | Godschalx et al. |
| 6,433,359 | B1 | 8/2002 | Kelley et al. |
| 2003/0094959 | A1 | 5/2003 | Hoisington et al. |
| 2003/0102471 | A1 | 6/2003 | Kelley et al. |
| 2003/0105365 | A1 | 6/2003 | Smith et al. |
| 2003/0150384 | A1 | 8/2003 | Baude et al. |

FOREIGN PATENT DOCUMENTS

| | | |
|---|---|---|
| EP | 0 275 075 A2 | 7/1988 |
| EP | 0 744 406 A2 | 11/1996 |
| WO | WO 93/09079 * | 5/1993 |
| WO | WO 93/09079 A1 | 5/1993 |

OTHER PUBLICATIONS

C. D. Sheraw et al., "Organic Thin-Film Transistor-Driven Polymer-Dispersed Liquid Crystal Displays on Flexible Polymeric Substrates", Applied Physics Letter, (Feb. 11, 2002), pp. 1088-1090, vol. 80, No. 6, American Institute of Physics, Melville, NY.

C. D. Dimitrakopoulos, et al., "Organic Thin Film Transistors for Large Area Electronics", Advanced Materials, (Jan. 16, 2002), pp. 99-117, vol. 14, No. 2, WILEY-VCH-Verlag GmbH, D-69469 Weinheim, Germany.

A. Kraft, "Organic Field-Effect Transistors—The Breakthrough at Last", CHEMPHYSCHEM, (2001), pp. 163-165, vol. 2, WILEY-VCH-Verlag GmbH, D-69451, Weinheim, Germany.

S. J. Martin, "Development of a Low-Dielectric-Constant Polymer for the Fabrication of Integrated Circuit Interconnect", Advanced Materials, (Dec. 1, 2000), pp. 1769-1778, vol. 12, No. 23, WILEY-VCH-Verlag GmbH, D-69469, Weinheim, Germany.

(Continued)

Primary Examiner—Johann Richter
Assistant Examiner—Chukwuma Nwaonicha
(74) Attorney, Agent, or Firm—Kent S. Kokko

(57) ABSTRACT

Bis(2-acenyl)acetylene compounds that are useful as organic semiconductors are disclosed. The compounds, when used as the active layer in OTFTs exhibit device characteristics, like charge-carrier mobilities and current on/off ratios, that are comparable to those of pentacene. Also described are semiconductor devices comprising at least one compound of the invention; and articles comprising the semiconductor devices such as thin film transistors or transistor arrays, and electroluminescent lamps.

25 Claims, 4 Drawing Sheets

OTHER PUBLICATIONS

C. D. Sheraw, "Spin-On Polymer Gate Dielectric for High Performance Organic Thin Film Transistors", Mat. Res. Soc. Symp. Proc., (2000), pp. 403-408, vol. 558, Materials Research Society.

P. Van Zant, "Microchip Fabrication", (2000), 4th Edition, McGraw-Hill, NY.

S. M. Sze, "Physics of Semiconductor Devices", (1981), pp. 492-493, 2th Edition, John Wiley & Sons, NY.

K. Ito, "Oligo(2,6-anthrylene)s: Acence-Oligomer Approach for Organic Field-Effect Transistors", Angewandte Chemie International Edition, (2003), pp. 1159-1162, vol. 42, No. 10, WILEY-VCH-Verlag GmbH & Co. KGaA, Weinheim, Germany.

H. E. Katz, "Synthetic Chemistry for Ultrapure, Processable, and High-Mobility Organic Transistor Semiconductors", Accounts of Chemical Research, (May 2001), pp. 359-369, vol. 34, No. 5, Amercian Chemical Society, Washington, DC.

"Organic Reactions", (1997), vol. 50, John Wiley & Sons, Inc., NY.

A. F. Littke et al., "Pd/P(t-Bu)$_3$: A Mild and General Catalyst for Stille Reactions of Aryl Chlorides and Aryl Bromides", Journal of the American Chemical Society, (Jun. 5, 2002), pp. 6343-6348, vol. 124, No. 22, American Chemical Society, Washington, DC.

J. E. Banks, "Cyclic Hydrocarbons and Substituted Hydrocarbons", Naming Oragnic Compounds, (1976), p. 124, 2nd Edition, W. B. Saunders Co., Philadelphia, PA.

D. J. Gundlach et al., "Solvent-Induced Phase Transition in Thermally Evaporated Pentacene Films", Applied Physics Letters, (May 31, 1999), pp. 3302-3304, vol. 74, No. 22, American Institute of Physics, Melville, NY.

H. Klauk et al., "High-Mobility Polymer Gate Dielectric Pentacene Thin Film Transistors", Journal of Applied Physics, (Nov. 1, 2002), pp. 5259-5263, vol. 92, No. 9, American Institute of Physics, Melville, NY.

D. Knipp et al., "Pentacene Thin Film Transistors on Inorganic Dielectrics: Morphology, Structural Properties, and Electronic Transport", Journal of Applied Physics, (Jan. 1, 2003), pp. 347-355, vol. 93, No. 1, American Intstitute of Physics, Melville, NY.

T. W. Kelley et al., "High-Performance OTFTs Using Surface-Modified Alumina Dielectrics", Journal of Physical Chemistry, (Jun. 19, 2003), pp. 5877-5881, vol. 107, No. 24, American Chemistry Society.

H. Sirringhaus et al., "Mobility Enhancement in Conjugated Polymer Field-Effect Transistors Through Chain Alignment in a liquid-Crystalline Phase", Applied Physics Letters, (Jul. 17, 2000), pp. 406-408, vol. 77, No. 3, American Institute of Physics, Melville, NY.

U.S. Appl. No. 10/434,377, filed May 8, 2003, entitled "Organic Polymers, Electronic Devices, and Methods".

U.S. Appl. No. 10/328,461, filed Dec. 23, 2002, entitled "AC Powered Logic Circuitry".

Liu et al., "Photophysical Behaviors of Oligomer Based on 1,1'-Binaphthol with 3,3'-Acetylene Spacer", Chinese Journal of Polymer Science, (1998), pp. 234-240, vol. 16, No. 3.

Schmidt et al., "2,2'-(Ethynediyl) bis(4-alkoxy-1-naphthols) and Dinaphthofuro[3,2-b] furans—Substances with Unusual Photoreactivity and Photochromic Behavior", Angew. Chem. Int. Ed. Engl., (1991), pp. 866-867, vol. 30, No. 7.

Murai et al., "Development of Novel Heterobimetallic Catalyst Using Linked BINOL as a Ligand and its Application to Tandem Henry Reaction", pp. 60-61, The Institute of Scientific and Industrial Research, Osaka University, Japan.

Hird et al., "The Synthesis and High Optical Birefringence of Nematogens Incorporating 2,6-disubstituted Naphthalenes and Terminal Cyano-Substituents", Liquid Crystals, (1993), pp. 123-150, vol. 15, No. 2.

Meng et al., "Stepwise Synthesis and Characterization of Oligomers Based on 1,1'-binaphthol with 3,3'-acetylene Spacer", Tetrahedron: Asymmetry 9 (1998), pp. 3693-3707, Elsevier Science Ltd.

Li, et al., "Palladium Catalysed Polymerization of Aryl Diodides with Acetylene Gas in Aqueous Medium: A Novel Synthesis of Areneethynylene Polymers and Oligomers", Chem. Commun., (1997) pp. 1569-1570.

Tayama et al., "Activation of Ether Functionality of Allyl Vinyl Ethers by Chiral Bis(organoaluminum) Lewis Acids: Application to Asymmetric Claisen Rearrangement", Tetrahedron 58, (2002), pp. 8307-8312, Elsevier Science Ltd.

Wang et al., "Enantiometric Discrimination of Chiral Amines with New Fluorescent Chemosensors", Chem. Commun., (1998), pp. 1747-1748.

Yin et al., "A Synthesis of Trisquinones", J. Org. Chem., (1998), pp. 5726-5727, vol. 63, American Chemical Society.

* cited by examiner

BIS(2-ACENYL)ACETYLENE SEMICONDUCTORS

FIELD

This invention relates to organic compounds that are useful as semiconductors and, in another aspect, to devices comprising the compounds, and to methods of preparing devices comprising the compounds.

BACKGROUND

Traditionally, inorganic silicon and gallium arsenide semiconductors, silicon dioxide insulators, and metals such as aluminum and copper have dominated the semiconductor industry. In recent years, however, there has been an increasing research effort in using organic thin-film transistors (OTFTs) as an alternative to the traditional devices based on inorganic material sets. Among other benefits, the use of organic materials may enable lower cost manufacturing of electronic devices, large area applications, and the use of flexible circuit supports for display backplanes or integrated circuits.

A variety of materials have been considered as organic semiconductors, with the most common being fused acenes as exampled by tetracene and pentacene, oligomeric materials containing thiophene or fluorene units, and polymeric materials like regioregular poly(3-alkylthiophene). While polymers may be coated from solution, device performance is poor when compared to well-ordered thin films prepared by high vacuum vapor deposition. Positive charge-carrier mobility (p-type) as high as 3.3 cm$^2$ V$^{-1}$ s$^{-1}$ (Kelley, T. W.; Boardman, L. D.; Dunbar, T. D.; Muyres, D. V.; Pellerite, M.; Smith, T. P. *J. Phys. Chem. B* 2003, 107, 5877–5881), on/off current ratios greater than 10$^8$ (Knipp, D.; Street, R. A.; Völkel, A.; Ho, J. *J. Appl. Phys.* 2003, 93, 347–355), and sub-threshold voltages of less than 0.5 V (Klauk, H.; Halik, M.; Zschieschang, U.; Schmid, G.; Radlik, W.; Weber, W. *J. Appl. Phys.* 2002, 92, 5259–5263), have been reported for pentacene-based transistors. These values are comparable or superior to those of amorphous silicon-based devices.

However, there are several areas where an alternative semiconductor material could offer improvements. The device architecture, choice of materials and substrate roughness all affect device performance. In pentacene-based devices, these variations have, in part, been attributed to the existence of several polymorphs. The alignment or structural order of the pentacene molecules differs for each polymorph or crystallographic phase, and this structural order determines the electronic properties of the device. The crystallographic phase adopted by pentacene depends on the process and conditions under which the crystals are formed. The thin film form of pentacene can be converted to the bulk phase by exposure to solvents such as isopropanol, acetone or ethanol. (See, for example, Gundlach et al., *Appl. Phys. Lett.*, 2000, 74(22) 3302.) Additionally, the long term oxidative and thermal stability of pentacene is unknown, as is the lifetime of pentacene-based semiconductor devices. The ease of synthesis and purification is another factor that must be considered in regard to the utility of an organic semiconductor. And lastly, it is likely that a variety of organic semiconductor materials possessing a range of physical and chemical properties may be required for specific applications.

SUMMARY

In view of the foregoing, we recognize there is a need for new organic semiconductors that provide stable and reproducible electrical characteristics.

Briefly, the present application discloses bis(2-acenyl) acetylene compounds that are useful as organic semiconductors. It has been discovered that the above-described compounds, when used as the active layer in OTFTs exhibit device characteristics, like charge-carrier mobilities and current on/off ratios, that are comparable to those of pentacene. The compounds of the present invention are reliably prepared, and purified to semiconductor grade by gradient sublimation at temperatures well below their decomposition point.

Thus, the disclosed compounds meet the need in the art for new organic semiconductors that provide useful performance and stability in devices and be viable alternatives to amorphous silicon or pentacene-based devices.

Also disclosed are semiconductor devices comprising at least one compound of the invention; and articles comprising the semiconductor devices. For example, specifically preferred devices include thin film transistors or transistor arrays, and electroluminescent lamps.

As used herein, "layer" refers to any layer that can be formed on a substrate from precursor compounds using a solution coating process or vapor deposition process, for example. The term "layer" is meant to include layers specific to the semiconductor industry, such as "barrier layer," "dielectric layer," "insulating layer," and "conductive layer." (The term "layer" is synonymous with the term "film" frequently used in the semiconductor industry.) The term "layer" is also meant to include layers found in technology outside of semiconductor technology, such as coatings on glass. "Dielectric layer" or "gate dielectric" as used herein refers to a layer (or film) having a relatively high dielectric constant.

DETAILED DESCRIPTION

Figure 1:
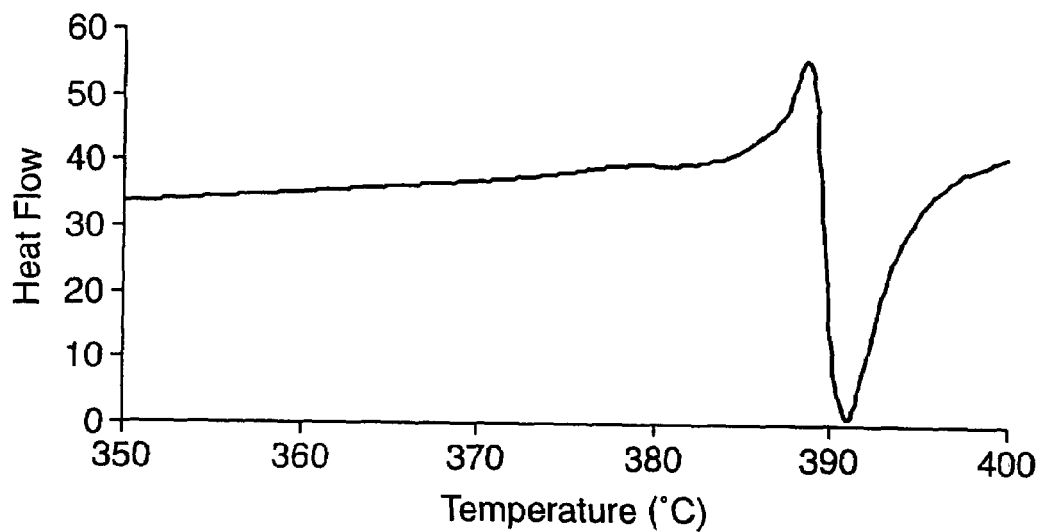
FIG. 1 is the differential scanning calorimetry plot of Example 2.

Bis(2-acenyl)acetylene compounds disclosed herein are useful as organic semiconductors. The compounds are of the general formula:

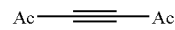

wherein each Ac group is independently selected from naphthalene (Np), anthracene (An), or tetracene (Tet). The Ac units are coupled through the 2-position of the acene ring to the central acetylide unit. The terminal ring, i.e the ring distal from the acetylide may be substituted or unsubstituted, and is preferably unsubstituted. Where substituted, symmetrical substitution is preferred, although it is recognized that asymmetric analogs may provide the same utility.

Compounds with fused aromatic ring systems are commonly given a numbering sequence in which each carbon atom that is a member of only one ring is numbered. (See, for example, James E. Banks, NAMING ORGANIC COMPOUNDS: A PROGRAMMED INTRODUCTION TO ORGANIC CHEMISTRY, Saunders College Publishing, p. 124, PA (1976).) The numbering sequence that is generally used for the acenes is shown below

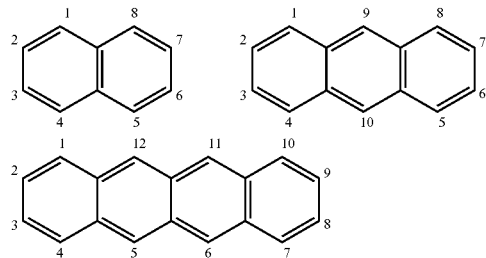

As previously noted, the acetylide moiety is attached to the 2-position of the acene ring system. The acene may be further substituted at the 5-, 6-, 7-, or 8-position of the naphthalene ring, the 5-, 6-, 7-, or 8-position of the anthracene ring, or the 7-, 8-, 9-, or 10-position of the naphthalene ring. The substituted acene compounds of the invention may comprise at least one substituent selected from the group consisting of electron-donating substituents, halogen substituents, and combinations thereof. Where the acene is substituted at the terminal ring, it is preferred that the substitution results in a symmetrical substitution, i.e. the 6-position of the naphthalene or anthracene rings, or the 8-position of the tetracene ring. One or both acene rings may be substituted.

Where present, each substituent is independently selected from the group consisting of alkyl groups, alkoxy groups, thioalkoxy groups, halogen atoms, and combinations thereof. More preferably, each substituent is independently an alkyl group, an alkoxy group, or a combination thereof. Most preferably, each substituent is independently an alkyl group. Useful alkyl groups, alkoxy groups, and thioalkoxy groups may include, for example $C_1$–$C_{18}$ alkyl groups, alkoxy groups, and thioalkoxy groups. At least some of the terminal ring substituted compounds of the invention are more soluble than pentacene in organic solvents and are therefore better candidates for economical solution processing methods of deposition.

It is most preferred that the terminal ring of the bis(2-acenyl)acetylene compounds are unsubstituted, due to the relative ease of synthesis.

Preferred compounds include, for example: bis(2-naphthyl)acetylene, bis(2-anthracenyl)acetylene, and bis(2-tetracenyl)acetylene, which may be substituted as described, but are preferably unsubstituted.

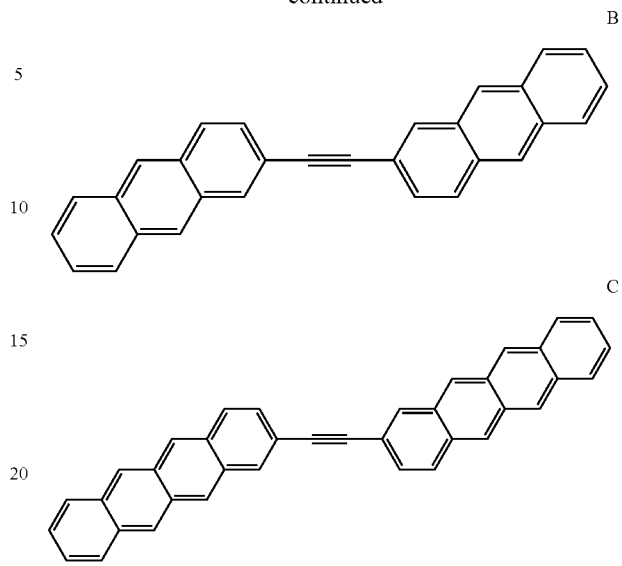

Preparation of Compounds

The bis(2-acenyl)acetylene compounds may be prepared by a Stille coupling of a 2-chloro- or 2-bromo acene with a bis(trialkylstannyl)acetylene. The Stille coupling may be performed as outlined by A. F. Littke et al., J. American Chem Soc., Vol 124, pp 6343–6348. Additional information regarding reaction conditions may be found in Farina, V.; Krishnamurthy, V., *Organic Reactions*; Paquette, L. A., Ed.; John Wiley & Sons, Inc., 1997; Vol. 50, p 1–652. The products may be purified to semiconductor grade by vacuum sublimation.

Other synthetic strategies can be employed to construct bis(2-acenyl)acetylenes. For example, a palladium catalyzed Suzuki coupling has been used to couple 2-bromoanthracene (see Ito, K.; Suzuki, T.; Sakamoto, Y.; Kubota, D.; Inoue, Y.; Sato, F; Tokito, S. Angew. Chem., Int. Ed. 2003, 42, 1159–1162). A review of synthetic methods for organic semiconductors has been recently published (see Katz, H. E.; Bao, Z.; Gilat, S. L. *Acc. Chem. Res.* 2001, 34, 359–369).

The terminal ring substituted bis(2-acenyl)acetylene compounds may be prepared by a Stille coupling of a terminal ring-substituted 2-chloro- or 2-bromo acene, such as 2-halo-6-alkyl naphthalene or anthracene, or the 2-halo, 8-alkyl tetracene, with a bis(trialkylstannyl)acetylene. The terminal ring-substituted 2-chloro- or 2-bromo acenes may be prepared by methods known in the art, and reference may be made to the synthetic schemes described in Applicant's copending application U.S. Ser. No. 10/256,616, published as U.S. 2003-0105365, and incorporated herein by reference.

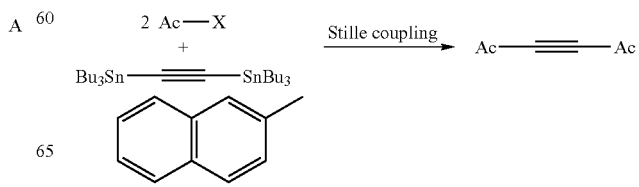

where Ac = 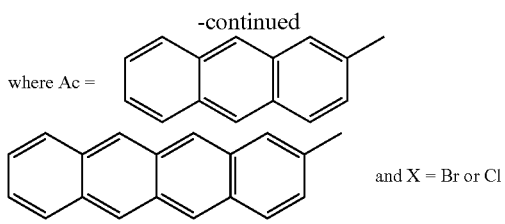 and X = Br or Cl

The disclosed compounds can be used as the semiconductor layer in semiconductor devices. Although there are numerous types of semiconductor devices, common to all is the presence of one or more semiconductor materials. Semiconductor devices have been described, for example, by S. M. Sze in *Physics of Semiconductor Devices*, 2$^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes), photoconductors, current limiters, thermistors, p-n junctions, field-effect diodes, Schottky diodes, and other devices known in the art. In each semiconductor device, the semiconductor material is combined with one or more metals or insulators to form the device. Semiconductor devices can be prepared or manufactured by known methods such as, for example, those described by Peter Van Zant in *Microchip Fabrication*, Fourth Edition, McGraw-Hill, New York (2000).

Electronic devices include components such as transistors, arrays of transistors, diodes, capacitors, embedded capacitors, and resistors that are used to form circuits. Electronic devices also include arrays of circuits that perform an electronic function. Examples of these arrays, or integrated circuits, are amplifiers, receivers, transmitters, inverters, and oscillators.

Applications of these devices and arrays include radio frequency identification devices (RFIDs), smart cards, lamps, displays, and the like. The present invention is not limited by the type of device. Particularly preferred types of devices include thin film transistors.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, *Physics of Semiconductor Devices*, 2$^{nd}$ edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated or uncoated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material or a polymeric dielectric layer.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric.

Alternatively, the gate dielectric may comprise an organic polymeric dielectric layer. A number of organic polymers have been considered as dielectric materials. These include polyimides, parylene C, crosslinked benzocyclobutene, and cyanoethylpullulan. See, for example, C. D. Sheraw et al., "Spin-on polymer gate dielectric for high performance organic thin film transistors", Materials Research Society Symposium Proceedings v 558, Materials Research Society, Warrendale, Pa., USA, pages 403–408 (2000); U.S. Pat. No. 6,265,243 (Katz); and U.S. Pat. No. 5,347,144 (Garnier).

A preferred group of organic polymeric dielectrics comprise polymers having a cyano-functional portion and a portion that provides a relatively high dielectric constant to the overall polymer, which portions may be the same or different. The polymers can be homopolymers or copolymers. Copolymers are those polymers prepared from two or more different monomers and include terpolymers, tetrapolymers, and the like. The monomers can join to form random, block, segmented copolymers, as well as any of a variety of other structural arrangements.

Such polymeric dielectric may a substantially nonfluorinated organic polymer having repeat units of the formulas:

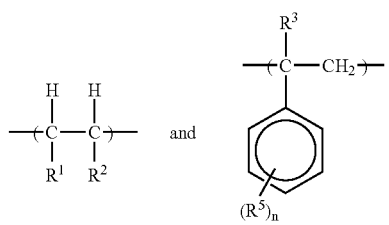

wherein: each $R^1$ is independently H, an aryl group (including aralkyl and alkaryl), Cl, Br, I, or an organic group that includes a crosslinkable group (i.e., one or more crosslinkable groups); each $R^2$ is independently H, an aryl group (including aralkyl and alkaryl), or $R^4$; each $R^3$ is independently H or methyl; each $R^5$ is a substituent on the aromatic ring and is independently an alkyl group, a halogen, or $R^4$;

n=0–3; and each $R^4$ is independently an organic group that includes at least one CN group and has a molecular weight of about 30 to about 200 per CN group; with the proviso that at least one repeat unit in the polymer includes an $R^4$. Preferably, at least one $R^1$ includes a crosslinkable group. The two repeat units could be the same, thereby forming a homopolymer. For certain embodiments, the substantially nonfluorinated dielectric polymer is crosslinked. Such polymers are disclosed in Applicant's copending application, U.S. Ser. No. 10/434,377, filed May 8, 2003 and is incorporated herein by reference.

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or ink jet printing. The patterning of these electrodes can be accomplished by known methods such as shadow masking, additive photolithography, subtractive photolithography, printing, microcontact printing, and pattern coating.

One particularly useful method of preparing thin film transistors or integrated circuits is by means of a flexible, repositionable polymeric aperture masks to create integrated circuits or integrated circuit elements. The techniques involve sequentially depositing material through a number of polymeric aperture masks formed with patterns that define layers, or portions of layers, of the circuit. In some embodiments, circuits can be created solely using aperture mask deposition techniques, without requiring any of the etching or photolithography steps typically used to form integrated circuit patterns. The techniques can be particularly useful in creating circuit elements for electronic displays such as liquid crystal displays and low-cost integrated circuits such as radio frequency identification (RFID) circuits. In addition, the techniques can be advantageous in the fabrication of integrated circuits incorporating organic semiconductors, which typically are not compatible with photolithography or other wet processes.

In various embodiments, different repositionable aperture masks such as flexible aperture masks, free-standing aperture masks and polymeric aperture masks formed with patterns may be used to define a layer or a portion of a layer of an integrated circuit. Repositionable polymeric aperture masks may have a thickness of approximately between 5 and 50 microns or approximately between 15 and 35 microns. The various deposition apertures in the aperture masks may have widths less than approximately 1000 microns, less than approximately 50 microns, less than approximately 20 microns, less than approximately 10 microns, or even less than approximately 5 microns. Apertures of these sizes are particularly useful in creating small circuit elements for integrated circuits. Moreover, one or more gaps between deposition apertures may be less than approximately 1000 microns, less than approximately 50 microns, less than approximately 20 microns or less than approximately 10 microns, which is also useful in creating small circuit elements. Also, aperture masks that include a pattern having a width greater than approximately 1 centimeter, 25 centimeters, 100 centimeters, or even 500 centimeters are also described. Patterns having these widths can be useful in creating various circuits over a larger surface area as described in greater detail below. In some embodiments, layer may be deposited on a substrate through repositionable polymeric aperture masks.

Various laser ablation techniques may be used to facilitate the creation of polymeric aperture masks having patterns of deposition apertures. In addition, stretching techniques and other techniques may be used to facilitate alignment of flexible polymeric aperture masks. Furthermore, methods of controlling sag in aperture masks may be used which can be particularly useful in using masks that include a pattern that extends over a large width.

The aperture masks can provide a number of advantages. For example, the aperture masks can facilitate the creation of relatively small circuit elements using deposition processes. The aperture masks can facilitate circuit elements having widths less than approximately 1000 microns, less than approximately 50 microns, less than approximately 20 microns, less than approximately 10 microns, or even less than approximately 5 microns. Also, the aperture masks can facilitate the creation of relatively large circuit patterns, in some cases having circuit elements of the relatively small widths mentioned above that cover large areas (such as 10 square centimeters, 50 square centimeters, 1 square meter, or even larger areas). In addition, the aperture masks can reduce costs associated with circuit fabrication, and in the case of organic semiconductors, can even improve device performance. Polymeric aperture masks can be created using a laser ablation process that may be faster and less expensive than other techniques. Also, inexpensive polymeric materials can allow the polymeric masks to be disposable, although reusable embodiments are also described.

In addition, polymeric material may be well suited to be impregnated with magnetic material. In that case, the magnetic material may be used to reduce sag in the mask as described below. Furthermore, polymeric material is often stretchable, which allows the mask to be stretched to either reduce sag or to align the mask.

Further details may be made with reference to Applicant's copending U.S. Ser. No. 10/19699, published as 03-0094959-A1, incorporated herein by reference.

The present invention further provides a thin film transistor comprising a surface treatment layer disposed between the described organic semiconductor and the gate dielectric. The surface treatment layer may be selected from a nonfluorinated polymeric layer, a self-assembled monolayer or a siloxane polymeric layer. The surface treatment layer provides organic thin film transistors with one or more improvements over known devices, including improvements in properties such as threshold voltage, subthreshold slope, on/off ratio, and charge-carrier mobility. In addition, large improvements in at least one property, such as charge-carrier mobility, can be achieved with the surface treatment layer, while maintaining other OTFT properties within desirable ranges. The improvements in device performance provided by the present invention enable the production by simpler processing conditions of complex circuits having higher operating speeds than an OTFT made without the surface treatment layer. This surface treatment layer also enables the production of larger circuit elements having comparable performance to devices with very small features. Devices with larger feature sizes can be less expensive as they do not require expensive precision patterning methods.

Any known thin film transistor configuration may be used with the surface treatment layer. For example, the source and drain electrodes may be adjacent to the gate dielectric with the organic semiconductor layer over the source and drain electrodes, or the organic semiconductor layer may be interposed between the source and drain electrodes and the gate dielectric. In each embodiment, the thin film transistor may include a surface treatment layer between the organic semiconductor layer and the gate dielectric.

In one embodiment, the present invention provides an organic thin film transistor (OTFT) comprising a substantially nonfluorinated polymeric layer interposed between a gate dielectric and the organic semiconductor layer of the invention, the substantially nonfluorinated polymeric layer having a thickness less than about 400 Å.

In one embodiment, the present invention provides a method of making an OTFT comprising providing a substrate, forming a gate electrode on the substrate, forming a gate dielectric on the gate electrode, applying a substantially nonfluorinated polymeric layer (having a thickness less than about 400 Å) interposed between the gate dielectric and an organic semiconductor layer, depositing an organic semiconductor layer adjacent to the polymeric layer, and depositing a source electrode and a drain electrode contiguous to the organic semiconductor layer. An integrated circuit comprising a plurality of OTFTs is also provided.

The polymeric surface treatment layer has a maximum thickness less than about 400 Angstroms (Å), more preferably less than about 200 Å, and most preferably less than about 100 Å. The polymeric surface treatment layer generally has a thickness of at least about 5 Å, more preferably at least about 10 Å. The thickness can be determined through known methods, e.g., ellipsometry.

The polymeric surface treatment layer is selected from many options. For example, a substantially nonfluorinated polymeric layer having a thickness within the range set forth above may be used. In this document, "substantially nonfluorinated" means that less than about 5% (more preferably less than about 1% and even more preferably 0%) of the carbons in the polymeric layer have fluorine substituents.

As used herein, "substituted" means substituted by substituents that do not interfere with the desired performance of the OTFT. Examples of suitable substituents include halogen (e.g., Cl, Br, I), cyano, $C_1$–$C_{20}$ aliphatic, aryl, and arylalkyl groups, and the like. As used in this document, "heteroatom" means a non-carbon atom such as O, P, S, N and Si.

The polymeric layer may comprise a polymer having interpolymerized units according to the formula:

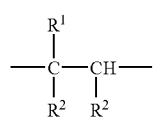
(I)

in an amount from about 50 to 100% of interpolymerized units according to Formula I, and from 0 to about 50% of said interpolymerized units according to the formula:

In these formulas, each $R^1$ and $R^2$ comprises, independently, a group selected from hydrogen; $C_1$–$C_{20}$ aliphatic; chloro; bromo; carboxy; acyloxy; nitrile; amido; alkoxy; carboalkoxy; aryloxy; chlorinated aliphatic; brominated aliphatic; $C_6$–$C_{20}$ aryl; $C_7$–$C_{20}$ arylalkyl; hydroxy when $R_1$ and X are different; and combinations thereof which may contain one or more heteroatom(s) and/or one or more functional group(s). Each X, independently, comprises a functional group capable of bonding to the gate dielectric. In addition, any combination of at least two $R^1$, $R^2$, and/or X groups may together form a cyclic or polycyclic, aliphatic or aromatic group.

Particular selections for $R^1$ and/or $R^2$ include groups selected from hydrogen, $C_1$–$C_{20}$ aliphatics, which may be linear or branched, saturated or unsaturated; $C_6$–$C_{20}$ aryl; and $C_7$–$C_{20}$ arylalkyl which also may contain linear or branched, and saturated or unsaturated segments. Specific polymers may be derived from precursor monomers such as methyl(meth)acrylate, straight-chain or branched $C_2$–$C_{18}$ aliphatic or arylalkyl(meth)acrylates, (meth)acrylic acid, (meth)acrylonitrile, 2-hydroxyethyl(meth)acrylate, vinyl chloride, vinyl acetate, ethylene, straight-chain or branched $C_3$–$C_{18}$ α-olefins, isoprene, chloroprene, 1,3-butadiene, diethyl fumarate, allyl acetate, methyl vinyl ketone, and styrene.

The functional group capable of bonding to the gate dielectric includes groups known to form chemical bonds to the selected gate dielectric. Particular selections for X groups include —$PO_3R_2$ or —$OPO_3R_2$ wherein each R is, independently, hydrogen or a $C_1$–$C_{12}$ aliphatic group or a $C_6$–$C_{18}$ aryl or arylalkyl group; —$SO_3H$; alkoxysilyl; chlorosilyl; acetoxysilyl; benzotriazolyl (—$C_6H_4N_3$); —CONHOH; —COOH; —OH; —SH; —COSH; —COSeH; —$C_5H_4N$; —SeH; —NC; amino; and phosphinyl. Benzotriazolyls include, for example, benzotriazolylcarbonyloxy (—OC(=O)$C_6H_4N_3$), benzotriazolyloxy (—O—$C_6H_4N_3$), and benzotriazolylamino (—NH—$C_6H_4N_3$) groups. Specific preferred groups include —$PO_3H_2$, —$OPO_3H_2$, and trimethoxysilyl.

Combinations of at least two $R^1$, $R^2$, and/or X groups may together form a cyclic or polycyclic group that can be aliphatic or aromatic. Specific examples are copolymers incorporating comonomers such as norbornene and substituted norbornenes, maleic anhydride, acenaphthylene, and itaconic anhydride. Also useful are polymers and copolymers which can form crosslinked networks by vinyl-type polymerizations, including those derived from divinylbenzenes, and (meth)acrylate-derived cinnamates.

Thus, the polymeric layer having interpolymerized units of Formula I and, optionally, Formula II, includes a broad array of materials. Specific examples include homopolymers such as polystyrene, poly(1-hexene), poly(methyl methacrylate), poly(acenaphthylene), poly(vinylnaphthalene), poly(butadiene), poly(vinyl acetate), and those derived from α-methylstyrene, 4-tert-butylstyrene, 2-methylstyrene, 3-methylstyrene, and 4-methylstyrene. In such homopolymer examples, the polymeric layer comprises 0% of said interpolymerized units according to Formula II.

A preferred polymeric layer is comprised of a polymer having styrenic interpolymerized units. Styrenic interpolymerized units include those derived from styrene and substituted styrenes, such as α-methylstyrene, 4-tert-butylstyrene, 2-methylstyrene, 3-methylstyrene, 4-methylstyrene, 4-(phosphonomethyl)styrene, and divinyl benzene.

Copolymers, such as block, random, and alternating, are also useful in the polymeric layer described in this invention. Useful copolymers comprise interpolymerized units of Formula I and optionally Formula II. Preferred examples include copolymers of at least two different monomers selected from styrene, α-methylstyrene, 4-tert-butylstyrene, 2-methylstyrene, 3-methylstyrene, and 4-methylstyrene. Other preferred examples include those materials having units of Formula II. Specific examples of monomers useful to form Formula II units include vinylphosphonic acid and other phosphonic acid-containing comonomers such as 4-(phosphonomethyl)styrene, and trialkoxysilane-containing comonomers such as 3-(trimethoxysilyl)propyl methacrylate. Preferred examples include a variety of copolymers of styrene and vinylphosphonic acid, copolymers of styrene and other phosphonic acid-containing comonomers, copolymers of styrene and phosphonate-containing comonomers, copolymers of styrene and phosphate-containing comonomers, a copolymer of styrene and 4-(phosphonomethyl) styrene, a copolymer of styrene and trimethoxysilylpropyl methacrylate, and copolymers of styrene and silyl-containing comonomers.

A class of polymers useful in the present invention includes hydrocarbon olefin homo- and co-polymers of ethylene, propylene, and higher α-olefins. These olefins can be represented by the general structure —$CH_2CHR$—, wherein R is hydrogen or a $C_1$–$C_{10}$ (preferably $C_1$–$C_6$) aliphatic radical. Copolymers may comprise one or more ethylenically-unsaturated comonomers which are copolymerizable with such olefins. These include vinyl esters, such as vinyl acetate; acrylic and α-alkyl acrylic acids and their alkyl esters, amides, and nitriles, such as methyl methacrylate and acrylonitrile; vinyl aromatics, such as styrene and vinylnaphthalene; anhydrides and alkyl esters of maleic and fumaric acids; vinyl alkyl ethers; vinylpyridine; N-vinylcarbazole; and dienes, such as 1,3-butadiene.

Polymers useful for this invention may also be prepared by the introduction of functional groups. These can be provided through the use of a variety of materials, typically referred to as functional initiators, functional chain transfer agents, or functional chain terminators. Examples of these materials include phosphorus oxychloride, mercaptopropyltrialkoxysilanes, chlorotrialkoxysilanes, and tetrachlorosilane. The introduction of these species typically introduces a functional group at the end or midpoint of a polymer chain. Examples of useful polymeric species prepared using these reactants include α-(triethoxysilyl)propylthio polystyrene, and ω-(phosphonic acid) polystyrene.

The polymer surface treatment layer may be derived from a ring-opening polymerization. A wide variety of monomers may be used in this embodiment. Examples of suitable monomers include cyclic ethers, cyclic amides, cyclic amines, cyclic sulphides, and inorganic ring compounds such as phosphonitrilic chlorides. The repeat units of the polymer in these materials are joined by links similar to those found in the monomer, but rearranged to provide a linear rather than cyclic chain. These polymerizations may proceed by a variety of mechanisms. One specific type of ring-opening polymerization is a ring-opening metathesis polymerization, or ROMP. Suitable monomers that can be polymerized in this fashion include norbornenes, $C_4$–$C_{10}$ cyclic alkenes, and $C_4$–$C_{10}$ cyclic non-conjugated dienes. These ROMP monomers may be substituted with one or more $C_1$–$C_{20}$ straight-chain or branched aliphatic groups, aromatic groups, or arylalkyl groups, any of which may include one or more heteroatoms. As is known, aliphatic groups may be saturated or may contain one or more carbon-carbon multiple bonds, while arylalkyl groups contain both aliphatic and aromatic structures. Specific materials useful in this aspect of the invention include straight-chain or branched $C_1$–$C_{18}$ alkyl-substituted norbornenes, trialkoxysilyl-substituted norbornenes, esters of 5-norbornene-2-carboxylic acid, esters of 2-phosphono-5-norbornene, 1,4-cyclooctadiene, and dicyclopentadiene.

The polymeric surface treatment layer may be derived from monomeric precursors, monomers, and oligomers comprising an aromatic-functional segment. Such polymeric materials are found in the class of aromatic thermosets. A preferred class of aromatic thermosets is the polyarylenes, for example, polyphenylene and polynaphthalene. Such polyarylenes include polymers containing heteroatoms, for example, polyarylene ethers. Polyarylenes can be prepared in a variety of ways. One useful means of preparing polyarylene compositions is by applying suitable monomeric or oligomeric precursors to the dielectric layer and subsequently polymerizing these materials through exposure to an energy source, such as by heating or irradiation. A preferred class of oligomer is a low molecular weight aromatic thermosetting composition comprised of cyclopentadienone and acetylene-substituted materials. The molecular weight is sufficiently low to permit spin coating of these oligomers. Such materials are commerically available as SiLK™ resin from Dow Chemical Co., Midland, Mich. The SiLK™ resin is more fully described in "Development of a Low-Dielectric-Constant Polymer for the Fabrication of Integrated Circuit Interconnect", Martin, J. P., et al., Adv. Mater. 2000, 12(23), 1769–1778 and references therein, and U.S. Pat. Nos. 5,956,679 and 6,288,188, which are all herein incorporated by reference. The SiLK™ resin can be spin-coated onto surfaces and then subsequently cured by heating to form an insoluble polyarylene film.

Other useful oligomeric compositions are polyfunctional o-phenylethynyl-substituted aromatic monomers which crosslink upon exposure to an energy source, especially thermal radiation, to form polynaphthalenes. Other examples of classes of monomeric precursors that form aromatic thermoset polymers include: cinnamates, divinylbenzenes, diacetylenes, benzocyclobutenes, and substituted derivatives thereof.

Other preferred classes of polyarylenes are the parylenes (i.e., poly(p-xylylene) polymers) and the polyfluorenes. The parylenes are semicrystalline polymers prepared by simultaneous adsorption and polymerization of reactive p-xylylene monomers from their vapor onto a surface. The vapor deposition of the monomer and its polymerization results in the formation of a thin film of uniform thickness conformal to the substrate surface that is effectively free of pinholes. Useful parylenes include parylene N, parylene C, and parylene D.

In another aspect, useful polymers and copolymers of the surface treatment layer are substantially non-polar, glassy solids at room temperature. Preferably, the polymer comprises 80 mole % or more of alkyl, aryl, or arylalkyl monomer units, wherein said monomer units are substantially free of heteroatoms. The polymer has fewer than about 20 mole % of monomer units containing heteroatoms (more preferably, fewer than about 10 mole %). Furthermore, said polymer preferably has a glass transition temperature ($T_g$) measured in the bulk of at least about 25° C., more preferably of at least about 50° C., and most preferably at least about 100° C. Examples of these types of polymers include many of those described above, including linear and thermoset materials. Specific examples include polystyrene, polyfluorene, polynorbornene, poly(acenapthylene), and alkyl-substituted derivatives thereof, and functionalized copolymers. In addition, blends of two or more polymeric or copolymeric materials may be used.

In another aspect, the OTFT of the invention has a substantially nonfluorinated polymeric layer having a thickness less than about 400 Å and the OTFT has a charge carrier mobility at least 50% greater than the charge carrier mobility of a similar OTFT lacking the polymeric layer. In another aspect of the invention, the OTFT has a charge carrier mobility at least 0.02 cm$^2$/Vs, preferably at least 0.10 cm$^2$/Vs, more preferably at least 1.0 cm$^2$/Vs, greater than the charge carrier mobility of a similar OTFT lacking the polymeric layer. In this document, all charge carrier mobility values are room temperature values.

The polymers and copolymers useful in the surface treatment layer can be prepared by any known means, for example, by free-radical, ring-opening, anionic, cationic, or coordination polymerization of monomers such as those described above. The polymer may also be modified by subsequent reactions to introduce functional groups.

The polymeric surface treatment layer is provided on the gate dielectric by any known method. For example, the polymeric surface treatment layer can be provided through a coating process such as spray, spin, dip, knife, gravure, microcontact printing, ink jet printing, stamping, transfer printing, and vapor deposition. The polymeric surface treatment layer can be provided on the gate dielectric via a solvent-based or solventless method. Presently preferred routes to the polymeric layer include solvent-based methods. When a solution of a polymeric surface treatment layer precursor is provided on the gate dielectric layer, the solvent is removed by a method compatible with the materials involved, for example by heating.

In one embodiment, the source and drain electrodes are deposited adjacent to the gate dielectric before providing the polymeric layer. Then, the polymeric surface treatment layer is applied. After the layer comprising a polymer is complete, the organic semiconductor layer is deposited over the source and drain electrodes and over the polymeric layer adjacent to the gate dielectric. Before deposition of the semiconductor, the material deposited on the gate dielectric to provide the polymeric layer may be rinsed so the source and drain electrodes are essentially free of the polymeric layer. That is, less than about 5 Å of polymeric layer, more preferably less than 1 Å and most preferably no polymeric layer, is present on the source and drain electrodes.

Further details regarding the polymeric layer may be had with reference to Applicant's copending application U.S. Ser. No. 10/012,654, filed Nov. 5, 2001, and incorporated herein by reference.

The surface treatment layer may also comprise a substantially siloxane polymeric layer having a thickness less than about 400 Å interposed between a gate dielectric and an organic semiconductor layer in an OTFT. The polymeric surface treatment layer comprises a substantially nonfluorinated polymer having interpolymerized units according to the formula:

wherein each R comprises, independently, a group selected from hydrogen, $C_1$–$C_{20}$ aliphatic, $C_4$–$C_{20}$ alicyclic, arylalkyl, or aryl, and a combination thereof which may contain one or more heteroatom(s) and/or one or more functional group(s). As used in this document, "heteroatom" means a non-carbon atom such as O, P, S, N and Si. In this document, "substantially nonfluorinated" means that less than about 5% (more preferably less than about 1% and even more preferably 0%) of the carbons in the polymeric layer have fluorine substituents.

The polymeric surface treatment layer of the invention has a maximum thickness less than about 400 Angstroms (Å), more preferably less than about 200 Å, most preferably less than about 100 Å. The polymeric layer of the invention generally has a thickness of at least about 5 Å, more preferably at least about 10 Å. The thickness can be determined through known methods, e.g., ellipsometry.

Particular selections for R groups include, for example, methyl, phenyl, 2-phenylethyl, $C_2$–$C_{18}$ aliphatic groups, and functional group-containing moieties including, but not limited to, hydroxyl, vinyl, 5-hexenyl, hydrogen, chloro, 3-(meth)acryloxypropyl, 3-mercaptopropyl, 3-glycidoxypropyl, 2-(3,4-epoxycyclohexyl)ethyl, 3-aminopropyl, 3-acetoxypropyl, 3-chloropropyl, 3-carboxypropyl, 3-cyanopropyl, chlorophenyl, $C_1$–$C_6$ 2-(dialkylphosphono)ethyl.

Examples of useful polymeric materials include poly(dimethylsiloxane), poly(dimethylsiloxane-co-diphenylsiloxane), poly(methylphenylsiloxane-co-diphenylsiloxane), and poly(dimethylsiloxane-co-methylphenylsiloxane).

Siloxane polymers useful in the practice of this invention may be prepared by any of a number of methods familiar to those skilled in the art, including, for example, anionic, condensation, or ring-opening polymerization. Siloxane polymers useful for this invention may also be prepared with the introduction of functional end-groups or functional pendant groups. This may be accomplished through the use of functional monomers, functional initiators, or functional chain terminators, for example, the termination of an anionically polymerized polydiorganosiloxane with a chlorotrialkoxysilane. They may also be prepared by modification of existing siloxane polymers, for example, the reaction of an olefinically functional polydiorganosiloxane with a silicon hydride, e.g., trichlorosilane.

While this invention emphasizes the use of linear polydiorganosiloxanes in which each unit in the siloxane polymer is derived from a difunctional precursor, it is considered within the scope of this invention to employ polyorganosiloxanes that incorporate small amounts of siloxane units derived from trifunctional or tetrafunctional precursors. The number of trifunctionally- and tetrafunctionally-derived siloxane units should not exceed about 10 percent, preferably about 5 percent or less, of the total average number of siloxane units in the polymer.

Useful polymeric materials may additionally include block copolymers comprising blocks of Formula (I) connected with blocks of interpolymerized units derived from an ethylenically unsaturated monomer such as styrene, butadiene, or isoprene. In addition, blends of two or more polymeric or copolymeric materials may be used.

In another aspect, the present invention provides a method of making an OTFT comprising providing a substrate, forming a gate electrode on the substrate, forming a gate dielectric on the gate electrode, applying a substantially nonfluorinated polymeric layer having a thickness less than about 400 Å interposed between the gate dielectric and an organic semiconductor layer, depositing the instant organic semiconductor layer adjacent to the polymeric surface treatment layer, and depositing a source electrode and a drain electrode contiguous to the organic semiconductor layer. An integrated circuit comprising OTFTs is also provided.

The surface treatment layer may also comprise a self-assembled monolayer interposed between a gate dielectric and an organic semiconductor layer, the monolayer being a product of a reaction between the gate dielectric and a precursor to the self-assembled monolayer, the precursor comprising a composition having the formula:

$$X{-}Y{-}Z_n,$$

wherein

X is H or $CH_3$;

Y is a linear or branched $C_5$–$C_{50}$ aliphatic or cyclic aliphatic connecting group, or a linear or branched $C_8$–$C_{50}$ group comprising an aromatic group and a $C_3$–$C_{44}$ aliphatic or cyclic aliphatic connecting group;

Z is selected from $-PO_3H_2$, $-OPO_3H_2$, benzotriazolyl ($-C_6H_4N_3$), carbonyloxybenzotriazole ($-OC(=O)C_6H_4N_3$), oxybenzotriazole ($-O-C_6H_4N_3$), aminobenzotriazole ($-NH-C_6H_4N_3$), $-CONHOH$, $-COOH$, $-OH$, $-SH$, $-COSH$, $-COSeH$, $-C_5H_4N$, $-SeH$, $-SO_3H$, $-NC$, $-SiCl(CH_3)_2$, $-SiCl_2CH_3$, amino, and phosphinyl; and n is 1, 2, or 3 provided that n=1 when Z is $-SiCl(CH_3)_2$ or $-SiCl_2CH_3$.

In another aspect, the present invention provides a method of making a thin film transistor comprising the steps of providing a substrate, providing a gate electrode material on the substrate, providing a gate dielectric on the gate electrode material, providing a self-assembled monolayer (SAM) adjacent to the gate dielectric, the monolayer being a product of a reaction between the gate dielectric and a precursor to the self-assembled monolayer, providing the instant organic semiconductor layer adjacent to the monolayer, and providing a source electrode and a drain electrode contiguous to the organic semiconductor layer. The precursor is as described above with the organic thin film transistor article. An integrated circuit comprising organic thin film transistor articles is also provided.

Self-assembled monolayer precursors provide molecules that form self-assembled films, typically, monolayer films on the target surface. Self-assembled thin films are often prepared by coating a substrate of interest in a dilute solution of the self-assembling precursor or by exposure to a vapor phase containing the precursor, and allowing film formation to proceed. The precursor molecules form a generally organized molecular film on the substrate. Once formed, the film does not redissolve in the solvent from which it was deposited.

Generally, materials that form crosslinks independently of monolayer formation, which may be in competition with the adsorption or bonding reaction to the gate dielectric, such as trifunctional silanes, are not desired for the monolayer precursor of the present invention. However, materials that have functional groups effective to bond to the gate dielectric and have other groups that may form crosslinks after formation of the SAM can be used.

Herein, the reaction between any gate dielectric and a functional group within the self-assembled monolayer precursor is preferably a bonding interaction (e.g. covalent or ionic). Herein, a self-assembled monolayer refers to a monomolecular layer on the order of about 5 Angstroms to about 30 Angstroms thick.

In preferred embodiments, Y can be a saturated aliphatic group, an unsaturated aliphatic group, a saturated cyclic aliphatic group, and an unsaturated cyclic aliphatic group, or a combination thereof, each of which may be linear or branched. The monolayer precursor may comprise a composition of the formula: $CH_3(CH_2)_mPO_3H_2$ wherein m is an integer from 4 to 21.

Particular examples for the monolayer precursor include 1-phosphonooctane, 1-phosphonohexane, 1-phosphonohexadecane, and 1-phosphono-3,7,11,15-tetramethylhexadecane.

One member of a class of branched hydrocarbon monolayer precursors useful in the practice of the present invention is 1-phosphono-3,7,11,15-tetramethylhexadecane. Other members of this class include 1-phosphono-2-ethylhexane, 1-phosphono-2,4,4-trimethylpentane, and 1-phosphono-3,5,5-trimethylhexane. The 1-phosphono-3,7,11,15-tetramethylhexadecane can be prepared from a commercially available allylic alcohol precursor by reduction of the alkene double bond, conversion of the alcohol to the corresponding bromide, and then conversion of the bromide to the corresponding phosphonic acid. More specifically, 1-phosphono-3,7,11,15-tetramethylhexadecane can be obtained by reducing 3,7,11,15-tetramethyl-2-hexadecen-1-ol to 3,7,11,15-tetramethyl-1-hexadecanol, converting the 3,7,11,15-tetramethyl-1-hexadecanol to 1-bromo-3,7,11,15-tetramethylhexadecane, and then converting the 1-bromo-3,7,11,15-tetramethylhexadecane to 1-phosphono-3,7,11,15-tetramethylhexadecane. These synthetic transformations are accomplished using materials and methods familiar to those skilled in the art. Starting materials other than 3,7,11,15-tetramethyl-2-hexadecen-1-ol and individual reaction sequences other than that described above may also be used to synthesize 1-phosphono-3,7,11,15-tetramethylhexadecane, as well as other members of this class of branched hydrocarbon monolayer precursors, and the specifically exemplified monolayer precursor and method of preparation should not be construed as unduly limiting.

The compounds of the invention can be used alone or in combination as the organic semiconductor layer of the OTFT (or other semiconductor device). The layer can be provided by any useful means, such as, for example, vapor deposition and printing techniques.

The compounds of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

EXAMPLES

Objects and advantages of this invention are further illustrated by the following examples, but the particular materials and amounts thereof recited in these examples, as well as other conditions and details, should not be construed to unduly limit this invention.

Synthesis of 2-bromoanthracene

A 1-L, 3-necked flask was fitted with a distillation head and purged with $N_2$. The system was charged with 2-bromoanthraquinone (29.0 g, 101 mmol), cyclohexanol (350 mL), and aluminum tri-sec-butoxide (140 mL, 550 mmol). The mixture was heated and became deep amber as distillate was collected until the pot temperature was 162° C. The reaction was heated at 160° C. for 16 h and then cooled to room temperature. The mixture was mixed with tetrahydrofuran (100 mL) and poured onto a 2 L filter frit to isolate the black solid. The solid was stirred on the frit with 6 M HCl (100 mL) and then further washed with water (500 mL). The gray crude product was air-dried overnight. The solid was purified further by vacuum train sublimation (pressure ~5×10$^{-5}$ Torr) at a source temperature of 120° C. to afford 12.6 g (48%) of off-white product. DSC data: peak temp 220° C. ($\Delta H$=126 Jg$^{-1}$. IR (KBr, strong abs only): 892, 741, 474 cm$^{-1}$. $^1$H NMR (500 MHz, d$_6$-Me$_2$SO, internal TMS). δ 7.56 (m, 6 lines, 6-H, 8-H), 7.60 (dd, J=2.0, 9.0 Hz, 7-H), 8.09 (m, 1-H, 3-H, 4-H), 8.39 ('d', J=1 Hz, 9-H), 8.57 (s, 5-H), 8.63 (s, 10-H).

Synthesis of 2-chlorotetracene

A 2-necked, 500 mL round-bottomed flask was fitted with a distillation head and receiver, and charged with 2-chloro-5,12-tetracenequinone (11.5 g, 39.4 mmol), cyclohexanol (100 mL), and Al(O-sec-Bu)$_3$ (50 mL) under nitrogen. The mixture was heated until distillate began collecting in the receiver at a pot temperature of ca. 115° C. The distillation was continued until the temperature of the dark orange mixture reached 162° C., and the solution was then heated at 159° C. for 36 h. The mixture was cooled to 50° C., an equal volume of dry THF was added, and then it was heated up to 80° C. and stirred. The hot mixture was poured onto a 10–20 μm frit to isolate a bright orange solid that was washed with water (150 mL), 5% HCl (150 mL), and additional water (150 mL). The filtrate was mixed with some additional water and conc. HCL, stirred, and allowed to sit overnight. The solid was air-dried for a couple of hours to afford 5.04 g of material. Purification by high vacuum (pressure ~10$^{-5}$ Torr) train sublimation at 130–150° C. afforded 4.0 g of fluorescent orange product. An additional crop of crude material was isolated from the filtrate above and afforded another 1.37 g after sublimation. Net yield 52%. DSC (20° C./min): 361° C. ($\Delta H$=96 Jg$^{-1}$, decomp). EIMS: 262 ([M]$^+$, 100%), 226 ([M−HCl]$^+$, 23%). Anal. Calcd. for $C_{18}H_{11}Cl$: C, 82.3; H, 4.22. Found: C, 82.5; H, 4.27.

Example 1

Preparation of bis(2-anthracenyl)acetylene

Bis(tri-n-butylstannyl)acetylene was obtained from Frontier Scientific. Pd$_2$(dba)$_3$, P(t-Bu)$_3$ (10 wt % in hexanes), and CsF (99.9%) were purchased from Strem. The CsF was mulled to a fine powder and dried under vacuum overnight at 80° C. Toluene was distilled from sodium and stored protected from the atmosphere in a Straus flask. Manipulations were carried out under nitrogen using standard Schlenk techniques. A 250 mL vessel was successively charged with Pd$_2$(dba)$_3$ (19 mg, 0.021 mmol, 0.5% mol), CsF (1.42 g, 9.33 mmol, 2.2 eq), PhMe (20 mL), 2-bromoanthracene (1.09 g, 4.24 mmol), bis(tributylstannyl)acetylene (1.29 g, 2.13 mmol), and P(t-Bu)$_3$ (0.15 mL, 0.052 mmol, 1.2%), and the mixture stirred overnight at room temperature to yield a fine orange ppt in an amber solution. The solid was isolated on a filter frit, washed with water, and air dried. The orange crude product was purified by high vacuum train sublimation at a source temperature of 225–275° C. to afford 444 mg (55%) of bright yellow product. EIMS: 378 ([M]$^+$, 100%), 189 ([M]$^{2+}$, 19%). DSC (20° C./min): 378° C. ($\Delta H$=3.2 Jg$^{-1}$), 389° C. ($\Delta H$=57 Jg$^{-1}$); the last endotherm is immediately followed by a sharp exotherm due to decomposition. Excitation spectrum in CHCl$_3$, (monitoring the fluorescence emission at 418 nm): $\lambda_{max}$ (normalized intensity), 284 (0.80), 308 (0.51), 320 (1.0). Fluorescence Spectrum (350 nm excitation in CHCl$_3$): $\lambda_{max}$ (normalized intensity), 418 (1.0), 438 (0.82). Anal. Calcd. for $C_{30}H_{18}$: C, 95.2; H, 4.79. Found: C, 95.3; H, 4.98.

Example 2

The thermal properties of bis(2-anthracenyl)acetylene were investigated by differential scanning calorimetry (DSC) and thermal gravimetric analysis (TGA). The TGA data shows an onset of decomposition of around 370° C. A plot of the differential scanning calorimetry data is shown in FIG. 1. Data were collected by heating the material under a nitrogen atmosphere from 0° C. to 400° C. at 20° C./min. Bis(2-anthracenyl)acetylene melts at ca. 389° C.; the phase change is accompanied by decomposition as evidenced by the subsequent exotherm. Under high vacuum, bis(2-anthracenyl) acetylene may be sublimed at ca. 225° C., or well below the decomposition point of the material.

Example 3

Figure 4:
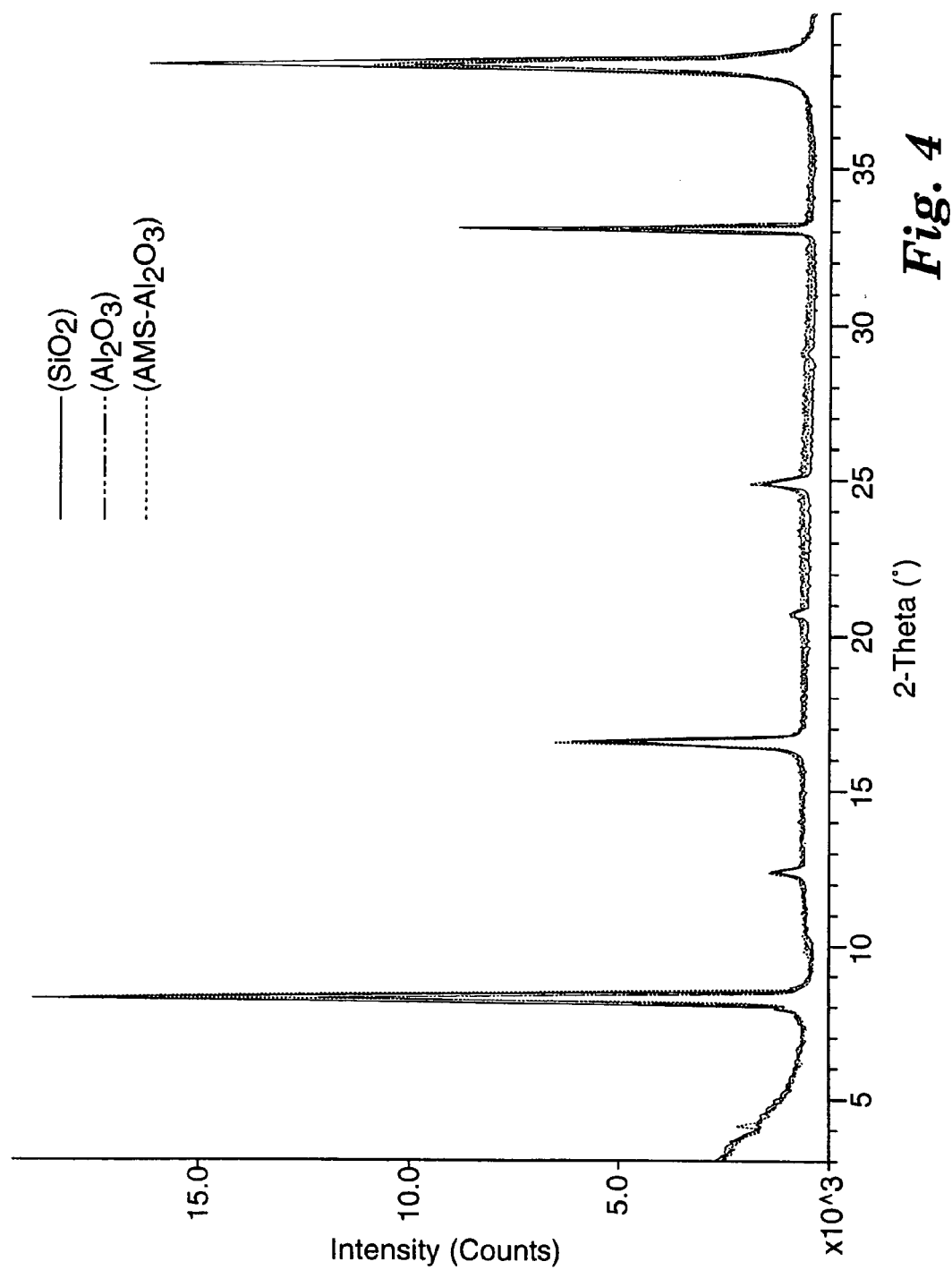
FIG. 4 is the x-ray diffraction data of Example 3.

X-ray diffraction patterns (Cu Kα radiation) for bis(2-anthracenyl)acetylene coated on 3 different substrates (SiO$_2$, Al$_2$O$_3$, and Al$_2$O$_3$ coated with 100 Å of poly(α-methylstyrene) [AMS-Al$_2$O$_3$]) are shown in FIG. 4. Each sample produced a series of (0,0,1) layer lines with spacings and intensities that are roughly independent of the substrate type. The spacing of 21.4 Å corresponds to the extended molecular length, and indicates that the molecules are oriented perpendicular to the substrate plane. It is this intermolecular arrangement that allows for good charge transport through the active channel when the TFT is in the on state. The well-ordered nature of the films is evident from the narrow and intense reflection lines.

Example 4

Figure 2:
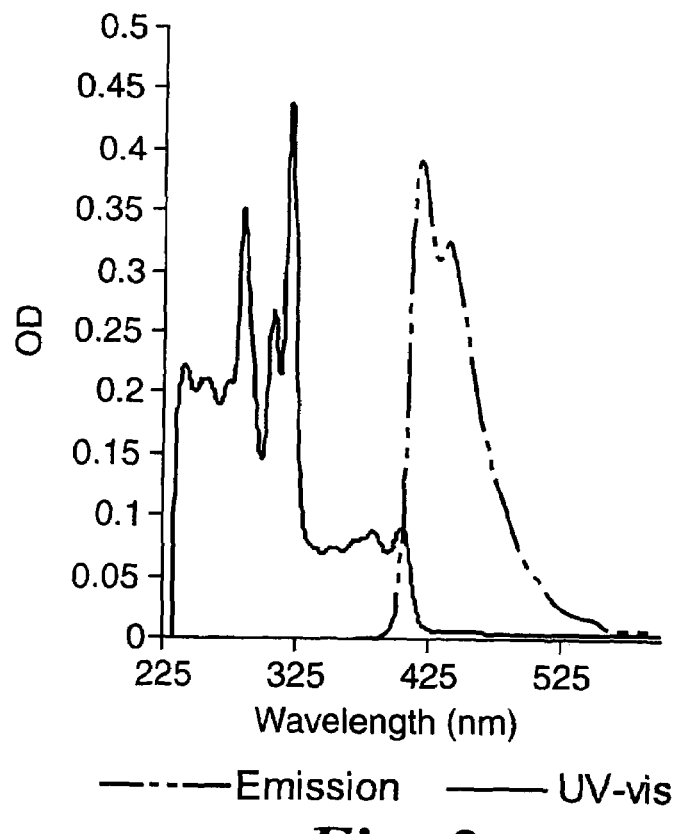
FIG. 2 is the absorbance and emission spectral data of Example 4.

Optical spectroscopic measurements using chloroform solutions of bis(2-anthracenyl) acetylene are shown in FIG. 2. The wavelengths of the absorbance and emission maxima are listed in Example 1. From the low energy side of the absorption maxima, a band gap of approximately 3.8 eV may be calculated, although low-level absorptions extend out to 425 nm. The high band gap of this material, as compared to pentacene for example (2.1 eV), could be advantageous in applications that require longer-lived and more stable electrical performance.

Example 5

Figure 3:
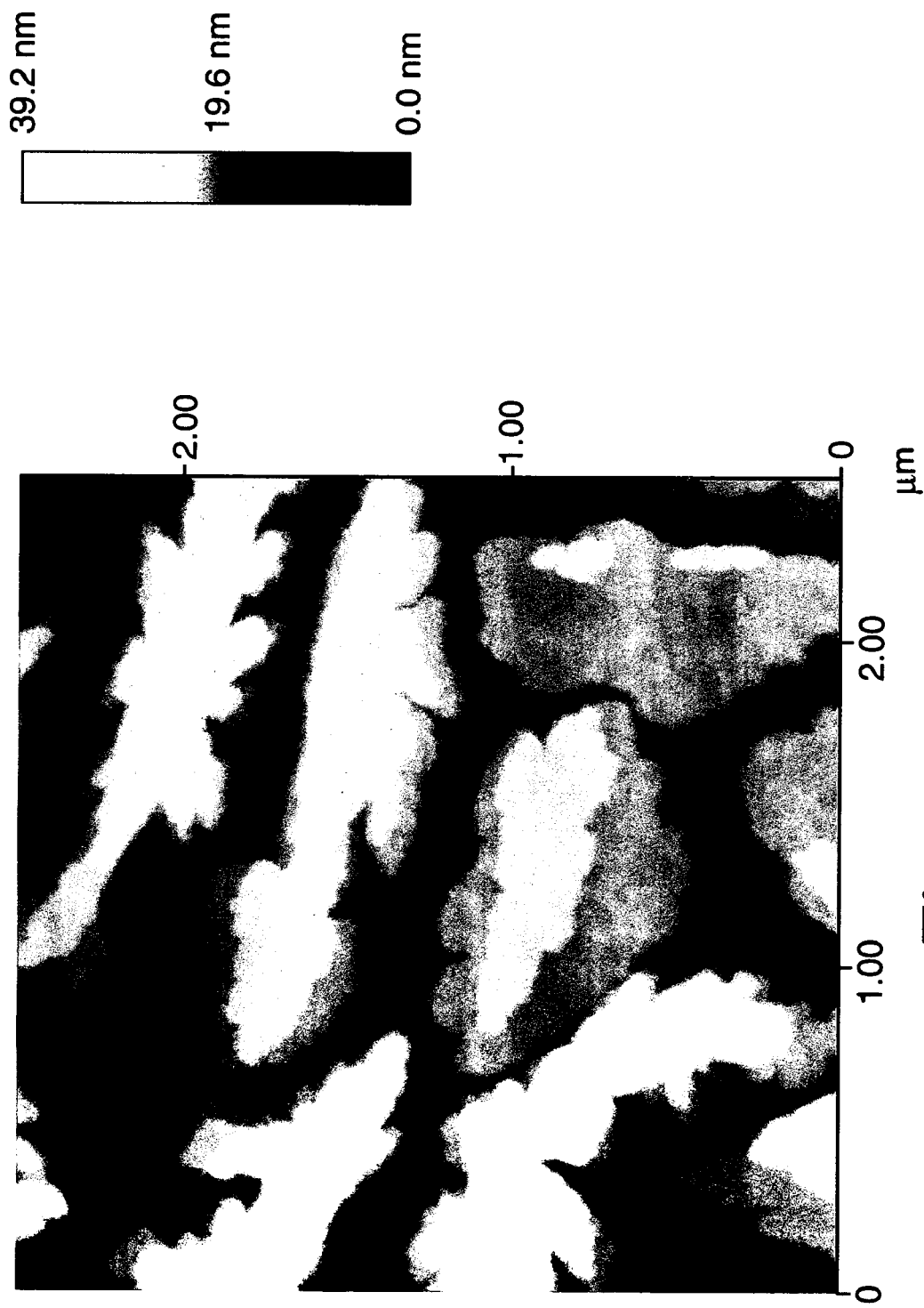
FIG. 3 is the digital image of the atomic force micrograph of Example 5.

An atomic force microscopy image of bis(2-anthracenyl) acetylene that was vacuum deposited at a rate of 0.5 Å/s on an Al$_2$O$_3$ substrate that was coated with poly(α-methylstyrene) is shown in FIG. 3. The thickness of the polymer surface treatment and semiconductor layers is ca. 300 Å and 100 Å, respectively. The crystals are on the order of 1–2 μm in size. It is well established in the art that crystallite size and quality can vary significantly with the substrate temperature during the deposition. No effort was made to control the substrate temperature during the deposition of the semiconductor materials.

Example 6

Figure 5:
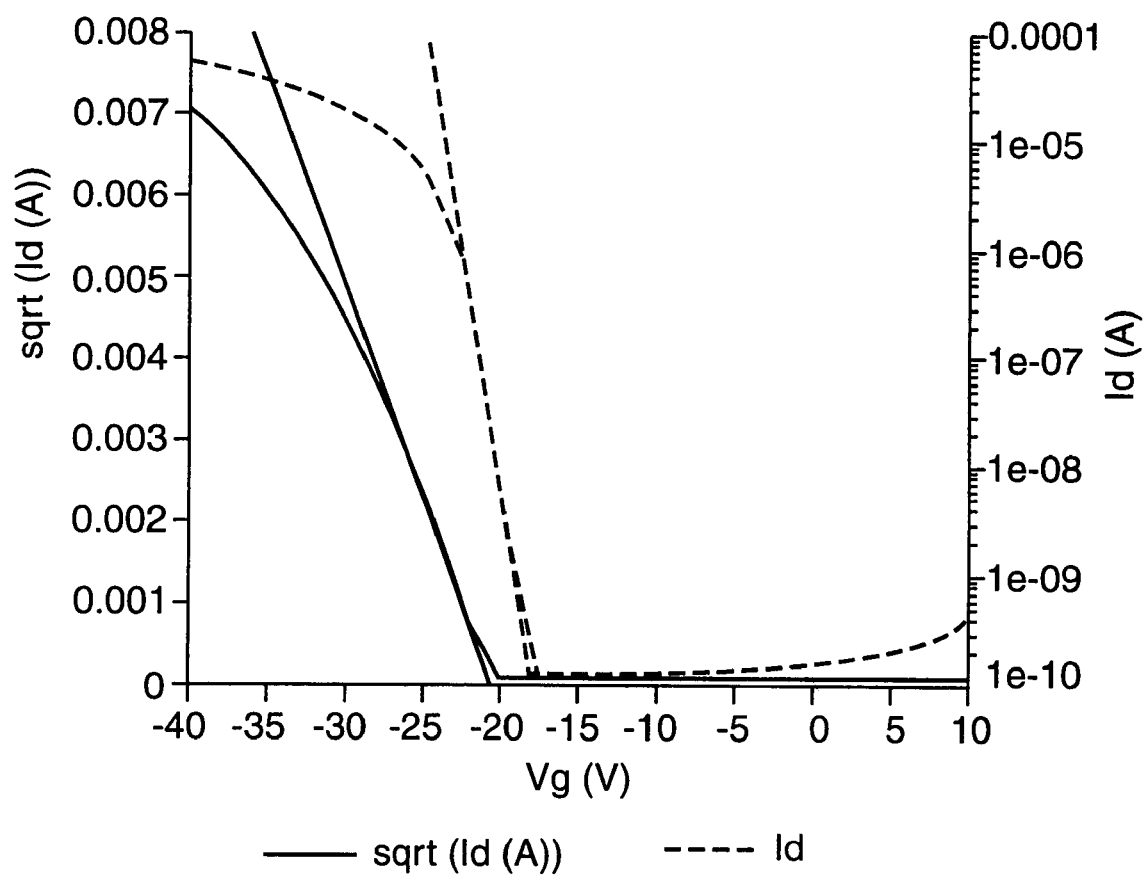
FIG. 5 is the transfer curve of Example 6.

TFTs were characterized using an HP Semiconductor Parameter Analyzer by sweeping the gate voltage, $V_g$ (+10 V to −40 V), and allowing the drain voltage, $V_d$, to remain constant at −40 V. A linear fit to the $I_d^{1/2}$–$V_g$ trace permits the extraction of saturation mobility and threshold voltage ($V_t$), and a linear fit to the $I_d$–$V_g$ trace allows the subthreshold slope (S) and the current on/off ratio to be calculated. FIG. 5 shows a representative device trace obtained under ambient conditions for a bis(2-anthracenyl) acetylene TFT constructed as described in example 5. The data for this sample were $\mu_{sat}$=1.1 cm$^2$/Vs, $V_t$=−21 V, S=1.1 V/decade, and $I_{on}/I_{off}$=4.4×10$^5$.

I claim:
1. Bis(2-acenyl)acetylene compounds of the formula:

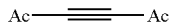

wherein each Ac group is independently selected from naphthalene, anthracene, or tetracene.
2. The compounds of claim 1 wherein each Ac group is tetracene.
3. The compounds of claim 1 wherein each Ac group is anthracene.
4. The compounds of claim 1 wherein each Ac group is napthalene.
5. The compounds of claim 1 wherein at least one of the terminal acene rings are substituted.
6. The compounds of claim 1 wherein both terminal acene rings are substituted.
7. The compounds of claim 6 selected from 6-substituted naphthalene rings, 6-substituted anthracene rings, or the 8-substituted tetracene rings.
8. The compounds of claim 5 where said substituents are selected from alkyl, alkoxy, thioalkoxy and halogen substituents.
9. The compounds of claim 1 wherein the terminal rings are unsubstituted.
10. A semiconductor device comprising at least one compound of claim 1.
11. The device of claim 10 wherein said device is an organic thin-film transistor.
12. The device of claim 10 wherein said device is an organic thin-film transistor comprising a surface treatment layer interposed between a gate dielectric and the semiconductor layer.
13. The device of claim 12 wherein said surface treatment layer is selected from a self-assembled monolayer, a non-fluorinated polymer layer or a siloxane polymer layer.
14. The device of 13 wherein the nonfluorinated polymer layer comprises a material selected from:
    a) a polymeric layer derived from monomeric precursors, monomers, and oligomers comprising an aromatic-functional segment;
    b) a polymeric layer derived from a ring-opening polymerization;
    c) a polymeric layer comprising a polymer having interpolymerized units according to the formula:

in an amount from about 50 to 100% of said interpolymerized units; and from 0 to about 50% of said interpolymerized units according to the formula:

wherein each $R^1$ and $R^2$ comprises, independently, a group selected from hydrogen; $C_1$–$C_{20}$ aliphatic; chloro; bromo; carboxy; acyloxy; nitrile; amido; alkoxy; carboalkoxy; aryloxy; chlorinated aliphatic; brominated aliphatic; $C_6$–$C_{20}$ aryl; $C_7$–$C_{20}$ arylalkyl; hydroxy when different $R_1$ and X groups are included; and combinations thereof which may contain one or more heteroatom(s) and/or one or more functional group(s);

each X, independently, comprises a functional group capable of bonding to the gate dielectric; and any combination of at least two $R^1$, $R^2$, and/or X groups may together form a cyclic or polycyclic aliphatic, aromatic, or polycyclic aromatic group; and d) combinations thereof.
15. The device of claim 13 wherein said siloxane polymer layer comprises a polymer having interpolymerized units according to the formula:

wherein each R comprises, independently, a group selected from hydrogen, $C_1$–$C_{20}$ aliphatic, $C_4$–$C_{20}$ alicyclic, arylalkyl, or aryl, and a combination thereof which may contain one or more heteroatom(s) and/or one or more functional group(s).
16. The device of claim 15 wherein the polymeric layer comprises poly(dimethylsiloxane), poly(dimethylsiloxane-co-diphenylsiloxane), poly(methylphenylsiloxane-co-diphenylsiloxane), or poly(dimethylsiloxane-co-methylphenylsiloxane).
17. The device of claim 13 wherein said surface treatment layer comprises a self-assembled monolayer interposed between a gate dielectric and an organic semiconductor layer, the monolayer being a product of a reaction between the gate dielectric and a precursor to the self-assembled monolayer, the precursor comprising a composition having the formula:

X—Y-Zn, wherein

X is H or $CH_3$;

Y is a linear or branched $C_5$–$C_{50}$ aliphatic or cyclic aliphatic connecting group, or a linear or branched $C_8$–$C_{50}$ group comprising an aromatic group and a $C_3$–$C_{44}$ aliphatic or cyclic aliphatic connecting group;

Z is selected from —$PO_3H_2$, —$OPO_3H_2$, benzotriazolyl (—$C_6H_4N_3$), carbonyloxybenzotriazole (—OC(=O)$C_6H_4N_3$), oxybenzotriazole (—O—$C_6H_4N_3$), aminobenzotriazole (—NH—$C_6H_4N_3$), —CONHOH, —COOH, —OH, —SH, —COSH, —COSeH, —$C_5H_4N$, —SeH, —$SO_3H$, —NC, —$SiCl(CH_3)_2$, —$SiCl_2CH_3$, amino, and phosphinyl; and n is 1, 2, or 3 provided that n=1 when Z is —$SiCl(CH_3)_2$ or —$SiCl_2CH_3$.

18. The device of claim 17 wherein the monolayer precursor comprises a composition selected from $CH_3(CH_2)_m PO_3H_2$, wherein m is an integer from 4 to 21.

19. The device of claim 18 wherein the monolayer precursor comprises a composition selected from 1-phosphonohexane, 1-phosphonooctane, 1-phosphonohexadecane, and 1-phosphono-3,7,11,15-tetramethylhexadecane.

20. A method of making an organic thin film transistor comprising:

a) providing a substrate;
b) depositing a gate electrode material on the substrate;
c) depositing a gate dielectric on the gate electrode material;
d) depositing an organic semiconductor layer comprising said bis(2-acenyl)acetylene of claim 1 adjacent to the polymeric layer; and
e) providing a source electrode and a drain electrode contiguous to the organic semiconductor layer.

21. The method of claim 20, further comprising the step of providing a surface treatment layer interposed between a gate dielectric and an organic semiconductor layer.

22. The method of claim 21 wherein said surface treatment layer is selected from a self-assembled monolayer, a nonfluorinated polymer layer or a siloxane polymer layer.

23. The method of claim 20 wherein said layers are deposited by means of one or more aperture masks.

24. The method of claim 23 wherein said aperture masks are polymeric aperture masks.

25. The method of claim 23 wherein said aperture masks are repositionable.

* * * * *